(12) United States Patent
Chamney et al.

(10) Patent No.: US 10,551,370 B2
(45) Date of Patent: *Feb. 4, 2020

(54) METHOD AND APPARATUS FOR EVALUATING VALUES REPRESENTING A MASS OR A CONCENTRATION OF A SUBSTANCE PRESENT WITHIN THE BODY OF A PATIENT

(71) Applicant: FRESENIUS MEDICAL CARE DEUTSCHLAND GMBH, Bad Homburg (DE)

(72) Inventors: Paul Chamney, Tring (GB); Ulrich Moissl, Karben (DE); Peter Wabel, Darmstadt (DE); Nestor Velasco, Glasgow (GB); Volker Nier, Reichelsheim (DE); Sebastian Weiskotten, Erfelden (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 358 days.

This patent is subject to a terminal disclaimer.

(21) Appl. No.: 15/049,641

(22) Filed: Feb. 22, 2016

(65) Prior Publication Data
US 2016/0169861 A1 Jun. 16, 2016

Related U.S. Application Data

(63) Continuation of application No. 13/394,997, filed as application No. PCT/EP2010/005480 on Sep. 7, 2010, now Pat. No. 9,301,716.

(30) Foreign Application Priority Data
Sep. 9, 2009 (EP) ................................. 09011550

(51) Int. Cl.
G01N 33/483 (2006.01)
A61B 5/00 (2006.01)
(Continued)

(52) U.S. Cl.
CPC ....... *G01N 33/483* (2013.01); *A61B 5/14542* (2013.01); *A61B 5/4839* (2013.01); *A61B 5/0537* (2013.01); *A61B 5/7264* (2013.01)

(58) Field of Classification Search
CPC . A61B 5/14542; A61B 5/4839; A61B 5/7264; A61B 5/0537
See application file for complete search history.

(56) References Cited

U.S. PATENT DOCUMENTS

| 4,895,163 A | 1/1990 | Libke et al. |
| 2004/0064063 A1 | 4/2004 | Chamney |

(Continued)

FOREIGN PATENT DOCUMENTS

| CN | 1573318 | 2/2005 |
| CN | 101102718 | 1/2008 |

(Continued)

OTHER PUBLICATIONS

International Search Report from PCT/EP2010/005480, dated Oct. 8, 2010. (cited and considered in parent U.S. Appl. No. 13/394,997).

*Primary Examiner* — Tiffany Weston
(74) *Attorney, Agent, or Firm* — Fish & Richardson P.C.

(57) ABSTRACT

The present invention relates to a method for evaluating a value representing the mass or the concentration of a substance comprised by a tissue or a bodily fluid of a patient, the method including the steps of a) determining a relation between one or more calculated or measured value(s) reflecting the mass or the concentration and a distribution space of the patient or an approximation thereof, and b) assessing whether the relation fulfils a criterion. The present (Continued)

invention further relates to systems and computer programs for performing this method.

24 Claims, 12 Drawing Sheets

(51) Int. Cl.
*A61B 5/145* (2006.01)
*A61B 5/053* (2006.01)

(56) References Cited

U.S. PATENT DOCUMENTS

| | | |
|---|---|---|
| 2004/0242977 A1 | 12/2004 | Dosmann |
| 2005/0102165 A1 | 5/2005 | Oshita et al. |
| 2006/0052764 A1 | 3/2006 | Gelfand et al. |
| 2006/0253016 A1 | 11/2006 | Baker, Jr. et al. |
| 2007/0118027 A1 | 5/2007 | Baker, Jr. et al. |
| 2008/0086058 A1 | 4/2008 | Chamney et al. |
| 2008/0194924 A1 | 8/2008 | Valk et al. |
| 2009/0137886 A1 | 5/2009 | Shariati et al. |
| 2010/0113891 A1* | 5/2010 | Barrett ............... A61B 5/14535 600/301 |

FOREIGN PATENT DOCUMENTS

| | | | |
|---|---|---|---|
| CN | 101309634 | 11/2008 | |
| CN | 101341391 | 1/2009 | |
| JP | H06218046 A | 8/1994 | |
| JP | H0951885 A | 2/1997 | |
| JP | H1014899 A | 1/1998 | |
| JP | 2004512128 A | 4/2004 | |
| JP | 2008504083 A | 2/2008 | |
| WO | 1999023938 A1 | 5/1999 | |
| WO | WO 99/23938 * | 5/1999 | ............... A61B 5/00 |
| WO | 2002053209 A1 | 7/2002 | |
| WO | 2008138062 A1 | 11/2008 | |
| WO | 2009115944 A1 | 9/2009 | |

\* cited by examiner

METHOD AND APPARATUS FOR EVALUATING VALUES REPRESENTING A MASS OR A CONCENTRATION OF A SUBSTANCE PRESENT WITHIN THE BODY OF A PATIENT

CROSS REFERENCE TO RELATED APPLICATIONS

This is a 371 national phase application of PCT/EP2010/005480, filed Sep. 7, 2010, claiming priority to European Patent Application No. 09011550.2, filed Sep. 9, 2009.

FIELD OF INVENTION

The present invention relates to a method for evaluating a value representing the mass or the concentration of a substance comprised by a tissue or a bodily fluid of a patient, the method comprising the steps of a) determining a relation between one or more calculated or measured value(s) reflecting the mass or the concentration and a distribution space of the patient or an approximation thereof, and b) assessing whether the relation fulfils a criterion. It relates further to a controller, an apparatus and a device for carrying out the present invention, further to digital storage means, a computer program product, and a computer program.

BACKGROUND OF THE INVENTION

In certain situations the mass or the concentration of a substance that is present in a patient's body has to be checked or monitored—e.g., by the physician in charge—be it for diagnostic reasons only or because the patient's state needs to be actively controlled by amending either concentration or mass of the substance. Hemoglobin (Hb) is such a substance among many others.

In practice, the concentration of hemoglobin (Hb, also known as Hgb, being the iron-containing oxygen-transport metalloprotein in the red blood cells) is measured by means of blood samples to assess the anemia state of the patient. Values below given thresholds are usually considered as a sign for the manifestation of "anemia" being defined as a decrease in normal number of red blood cells (RBCs) or less than the normal quantity of hemoglobin in the blood.

SUMMARY OF THE INVENTION

By means of the present invention a method of evaluating a value reflecting the mass or the concentration or the volume of a substance is suggested. Also, a controller for carrying out the method according to the present invention is provided, as well as an apparatus, a device comprising a controller, digital storage means, a computer program product, and a computer.

The method according to the present invention is defined by the feature combination of claim 1. Accordingly, in one aspect of the present invention, an evaluation—or a method for evaluating—of a value representing the mass or the concentration or the volume—or changes thereof, respectively—of a substance comprised by a tissue or a bodily fluid of a patient comprises the step of determining a relation between one or more calculated or measured value(s) reflecting the mass or the concentration or the volume of the substance comprised by the tissue or the bodily fluid on the one hand, and one or more calculated or measured value(s) reflecting a distribution space (or changes thereof) of the patient or an approximation thereof on the other hand, and assessing whether the relation fulfils at least one criterion.

The patient can be either a human being or an animal. The patient may be sound or ill. The patient may be in need of medical care or not.

The controller according to the present invention is defined by the feature combination of claim 17. Accordingly, in another aspect of the present invention, the controller is configured to carry out the method according to the present invention.

The apparatus according to the present invention is defined by the feature combination of claim 18. Accordingly, in another aspect of the present invention, the apparatus comprises means for obtaining a value representing the volume, the mass or the concentration of a substance and/or means for obtaining a value representing the distribution space, or changes thereof, respectively, and at least one controller according to the present invention.

The device according to the present invention is defined by the feature combination of claim 22 for treating the blood of a patient. Accordingly, in another aspect of the present invention, the device comprises at least one controller according to the present invention or at least one apparatus according to the present invention.

The digital storage means according to the present invention is defined by the feature combination of claim 25. Accordingly, in another aspect of the present invention, the digital storage means, in particular a disc, CD, or DVD, has electrically readable control signals which are able to interact with a programmable computer system such that a method according to the present invention will be executed.

The computer program product according to the present invention is defined by the feature combination of claim 26. Accordingly, in another aspect of the present invention, the computer program product has a program code stored on a machine readable data medium for executing a method according to the present invention when executing the program product on a computer.

The computer program according to the present invention is defined by the feature combination of claim 27. Accordingly, in another aspect of the present invention, the computer program has a program code for the execution of a method according to the present invention when executing the program on a computer.

It is noted that whenever it is referred to mass or concentration or volume of a substance in the present specification, changes thereof are also contemplated, be it expressly mentioned or not.

Embodiments can include one or more of the following features.

In some embodiments, a calculated or measured state reflecting both the mass—or the concentration of a substance—and a distribution space of the patient is a pair of values of the type "(x; y)" with x representing the mass or the concentration—or changes thereof—and y representing the distribution space. Preferably, both x and y results from measurements performed at the same time (e.g., same minute, same hour, same day, same week, same month, same stay or visit at the hospital, etc.)—or calculations based on results of such measurements.

In certain embodiments, the method includes using values reflecting the mass or the concentration that was obtained from at least one urine sample.

In some embodiments, the method includes using values reflecting the mass or the concentration that was obtained from at least one blood sample.

In certain embodiments, the blood sample has been taken from an extracorporeal blood circuit, in other embodiments from a blood vessel of the patient.

In some embodiments, the method includes using values reflecting the mass or the concentration that was obtained from at least one tissue sample or at least one saliva sample.

In certain embodiments, the values may also have been obtained from whole body measurements, or from part body measurements for measuring body contents directly (and not by means of indirect methods such as urinalysis).

In some embodiments, the whole body measurement is directed to the measurement of radioactive substances (such as, e.g., potassium) by means of a whole body counter as is known from the prior art. Upon such whole body measurement, the patient is isolated from the radioactive background activity by appropriate means such as a chamber shielding the patient positioned within the chamber from radioactive activity from outside. Knowing the activity of the radioactive substance to be measured, and also knowing the invariable or constant ratio between the radioactive substance and the non-radioactive substance comprised by the body of the patient, it is possibly to determine the whole body content of the substance in question.

In some embodiments, assessing whether the relation fulfils at least one criterion means determining whether or not the relation fulfils certain—predetermined or during executing the method according to the present invention determined—demands or requests (with "demand" and "request" being alternatives, examples or synonyms for "criteria" in the context of the present invention).

For example, when the relation is expressed in numbers, the criterion may be one or more threshold values, so that the relation fulfils the criterion if the number expressing the relation is higher (or lower) than a threshold, or between two or more thresholds. Similarly, when the relation is expressed as a symbol or a range or a curve in a graphic, the criterion may be expressed as a range in the graphic, so that to fulfil the criterion the relation may be above, in or below a predetermined range in a graphic, etc. These examples should, of course, not be understood to limit the present invention to these embodiments.

In certain embodiments, the relation may be a ratio of values. For example, it may be expressed by "concentration (or mass or change of concentration or change of mass)" over "distribution space (or an approximation of the distribution space)". In one embodiment, the relation is expressed by "concentration of Hb over relative overhydration", with relative overhydration being related to the distribution space.

In some embodiments, the distribution space is a body fluid. In certain embodiments, the distribution space is body tissue or the body weight or the total body mass. In other embodiments, the distribution space is not the body weight or not the total body mass. In some embodiments, the distribution space is a combination of a body fluid and a body tissue. In some embodiments, the distribution space is a space that comprises the substance at issue. In certain embodiments, the distribution space is the space where the major part of the substance at issue is found in the body of the patient. In some embodiments, the distribution space is the only space of the body of the patient where the substance at issue is found.

In certain embodiments, the distribution space is defined as the blood volume (BV). The distribution space may also be defined as the ECW (extracellular water), the extracellular volume or fluid or mass of the body, the ICW (intracellular water), the intracellular volume or fluid or mass of the body, the plasma volume, the TBW (total body water), the liquor, the volume of edema, lymph, urine, the total cell mass or any other bodily fluid or volume, and also combinations thereof. Also, the distribution space within the meaning of the present invention can be any ratio of volumes as mentioned before, e.g. ECW/ICW, etc.

In some embodiments, the distribution space is defined as the muscle mass or volume. It can also be defined as the fat mass or volume, the bone mass or volume, etc.

In certain embodiments, the mass or the concentration of the substance is an indicator of an anemia state of the patient.

The some embodiments, the indicator of an anemia state is the total mass or the concentration of hemoglobin (Hb) or changes thereof over time, etc.

In certain embodiments, the concentration or the mass is directly measured, e.g., from blood samples or by means of optical methods, e.g., without having drawn blood from a vessel as it is known in the art. In addition, or alternatively, the values at issue may be derived from other values, parameters, etc. which allow a correct calculation or at least a sufficient approximation of the substance, such as hemoglobin (Hb) or the hemoglobin (Hb) state.

In some embodiments, the indicator of an anemia state is the hematocrit (Hct), with the hematocrit (Hct) being understood also as a concentration within the present invention.

In certain embodiments, the anemia state of the patient is expressed by only one value such as a Hb concentration, or the Hct, etc.

In certain embodiments, the substance is comprised by the group comprising at least any protein produced naturally in the body of the patient, in particular hemoglobin, albumin, insulin, glucose, CRP, hormones, total protein; cells (e.g., leucocites), electrolytes, and non-endogenous substances, in particular pharmaceutically-effective substances like cytostatika, non-physiologic markers such as deuterium, etc.

In some embodiments, the distribution space is approximated based on measurements of the hydration state of the patient.

In certain embodiments, the distribution space is approximated, calculated or defined based on measured values and/or calculations reflecting the overhydration (OH) or the relative overhydration (relOH: overhydration (OH) over extracellular water (ECW)), etc. of the patient. As regards a definition of overhydration (OH) it is referred to in WO 2006/002685 A1, where OH equals $a*ECW + b*ICW + c*body\ weight$. The respective disclosure of WO 2006/002685 A1 is hereby incorporated by way of reference. It is to be understood that OH can be determined in different ways, all of which are known to the person skilled in the art. One of those methods comprises the measuring of a dilution and the calculation of OH based thereon.

What has been described with reference to hemoglobin (Hb) regarding concentration, change over time, values, calculation, approximation, etc. is meant to apply to the hematocrit (Hct), the blood volume (BV), the overhydration (OH), and the relative overhydration (relOH), as well.

In some embodiments, the distribution space of the patient may be expressed by an age corrected overhydration or relative overhydration (relAEOH). In doing so, certain effects, e.g. due to age, can be eliminated for achieving more relevant values.

In certain embodiments, the distribution space of the patient may be determined or defined as overhydration (OH) over extracellular water (ECW) or may be graphically displayed in this way.

In some embodiments, the distribution space of the patient is expressed by only one value, in particular a value having the dimension liter (L).

In certain embodiments, the distribution space is measured or approximated before dialysis or based on pre-dialysis values of the patient.

In some embodiments, pre-dialysis (pre-Dx) values or calculations may be data obtained immediately, i.e., moments or minutes, before starting the next dialysis treatment. The invention is, however, not limited to this. Data can also be obtained at any other point of time. Pre-Dx data appear to be more stable than others. Using them can therefore be of advantage.

In certain embodiments, a target range is defined in a diagram representing both the mass or the concentration or the volume of the substance of changes thereof, and the distribution space of the patient or an approximation thereof. The target range may alternatively be a target area. The diagram may alternatively be a plot. The diagram may be a Cartesian coordinate system, also called a "rectangular coordinate system." In a graphic illustration of the diagram, the mass or the concentration or the volume of the substance or changes thereof can be shown over the distribution space or vice versa.

In some embodiments, the criterion is a threshold or a combination of more than one threshold.

In certain embodiments, the at least one criterion is preset or predetermined.

In some embodiments, the at least one criterion is variable.

In certain embodiments, the method further includes determining the criterion.

In some embodiments, the criterion is determined during executing the method according to the present invention.

In certain embodiments, a regression line is calculated based on measured values or calculated results each reflecting both a mass (or a concentration or a volume or changes thereof, respectively) and a distribution space, and assessing a position between the regression line and the target range relative to each other. Relative to each other can be understood as "above", "below" besides", "within", "crossing" and so forth. The relative position can be attributed certain degrees or numeral value.

In some embodiments, the criterion can be based on a classification, in particular a Bayes-classification. Also, it is contemplated to define a criterion based on a Fuzzy-Logic. A classification may also be achieved by means of Nearest Neighbour, and by neural networks, etc.

In certain embodiments, a regression line is calculated based on measured values or calculated results. The regression line can express any appropriate function.

In some embodiments, the values for mass or concentration and for the distribution space are such obtained at one occasion. "One occasion" may be understood as a specific time, e.g. a range of a few minutes or hours. It may also be a day or the duration of one treatment, in particular one dialysis treatment. "One occasion" may also be understood as the time the patient spends in the clinic for treatment.

In certain embodiments, the method comprises classifying the results of the assessment.

In some embodiments, the method according to the present invention includes plotting or drawing the regression line and/or the target range where necessary.

In certain embodiments, the method includes displaying in a table, a spreadsheet or a chart, etc. whether the criterion has been fulfilled (or not).

In some embodiments, it is assessed whether or not the criterion is fulfilled based on only two values: one value reflecting the mass or the concentration of the substance and one value reflecting the distribution space.

In certain embodiments, the two values are represented by only one point in a appropriate graphic.

In some embodiments, the assessment may be carried out solely with that one point or those two values.

In certain embodiments, one or all values considered for determining the relation reflect the corresponding mass, volume, concentration in an absolute manner. That is, changes over time may remain unconsidered. Any value reflecting mass, concentration or volume may be, hence, a static one.

Also, in some embodiments, the value reflecting the mass, concentration or the volume of a substance is not arrived by subtracting of values, e.g., a first concentration value from a second concentration value, etc.

In certain embodiments, for determining the relation no time constant or time variable or parameter is considered or included. In particular, no mass, concentration or volume value is multiplied by a time value.

In some embodiments, the slope of a regression line is also considered upon the step of assessing. The slope may be estimated or may be (approximately) known from earlier measurements from the same patient or a corresponding patient or collective of patients (sound or ill).

In certain embodiments, the y-offset of a regression line is also considered upon the step of assessing. "y" may relate to the mass, concentration or volume of the substance, or to the hydration value, e.g. relOH when displayed in a diagram, e.g. in a Cartesian coordinate system.

In some embodiments, the value reflecting the distribution space is measured in liters (L).

In certain embodiments, the mass or the concentration (or changes thereof) and the distribution space of the patient are calculated and/or measured. The measurement and calculations may be carried out by means of any method known in the art, using any device suitable therefor. In particular, in some embodiments, the respective data may be obtained by measuring Hb from blood samples and/or from blood comprised in extracorporeal blood lines by means of an appropriate monitor. The measurements can be made by measuring the optical properties of the blood by optical sensors and/or by assessing acoustic properties like transit times and/or propagations velocities of ultrasonic pulses by ultrasonic sensors.

For determining the hydration state any appropriate monitor can be used, such as monitors based on bioimpedance or dilution techniques.

The monitor for obtaining data related to the hydration state can be a monitor as described in WO 2006/002685 A1. The respective disclosure of WO 2006/002685 A1 is hereby incorporated in the present application by way of reference. Of course, the present invention must not be understood to be limited to monitors determining the hydration state of the patient by bioimpedance measurements as is described in WO 2006/002685 A1. Other methods known in the art such as dilution measurements and also any other method known to the skilled person are also contemplated and encompassed by the present invention as well.

In some embodiments, a dosage of a medicament to be administered to a patient for improving his anemia state is determined or adjusted based on the result of assessing whether the criterion is fulfilled or not.

In certain embodiments, the distribution volume should be adjusted. This can be achieved by administration of substances such as diuretics and/or by dialysis, e.g. ultrafiltration. In some embodiments, a pharmaceutically effective substance is administered. In certain embodiments, the result of the assessment as regards the criterion is outputted in form of an advise of how to treat the patient.

In some embodiments, the criterion is set or determined or pre-determined.

In certain embodiments, the apparatus is a monitor for obtaining information concerning distribution space or an approximation thereof, e.g., the hydration state. An example of such a monitor is described above. For avoiding unnecessary repetition, it is generally referred to hydration monitors that yield results reflecting the hydration state based on bioimpedance signals, dilution methods or any other method known in the art.

In some embodiments, the apparatus comprises furthermore an output device for outputting results provided by the controller. The output device may be a monitor having a display, a plotter, a printer or any other means for providing an output.

In certain embodiments, the apparatus comprises a monitor for measuring Hb concentrations (e.g., in [g/dl]) and/or for determining the blood volume by means of any monitor as described in "*Replacement of Renal Function by Dialysis*" by Drukker, Parson and Maher, Kluwer Academic Publisher, 5$^{th}$ edition, 2004, Dordrecht, The Netherlands, on pages 397 to 401 ("*Hemodialysis machines and monitors*"), the respective disclosure of which is hereby incorporated by way of reference.

In some embodiments, the monitor is configured to measure the blood volume and/or the concentration of the substance—in particular Hb—by means of measuring an electrical conductivity.

In certain embodiments, the monitor is configured to measure the blood volume and/or the concentration of the substance—in particular Hb—by means of measuring an optical density.

In some embodiments, the monitor is configured to measure the blood volume and/or the concentration of the substance—in particular Hb—by means of measuring a viscosity.

In certain embodiments, the monitor is configured to measure the blood volume and/or the concentration of the substance—in particular Hb—by means of measuring a density.

In some embodiments, the monitor comprises one or more corresponding probes and/or one or more sensors for carrying out the measurements such as electrical conductivity sensors, optical sensors, viscosity sensors, density sensors, and the like.

In certain embodiments, the device may be used for treating a patient by means of dialysis.

In other embodiments, the device may be used for treating a patient (or the patient's blood) by hemofiltration, ultrafiltration, hemodialysis, etc.

The embodiments may provide one or more of the following advantages.

By means of the present invention, the merit of parameters or values representing certain states of the patient caused or accompanied by certain values reflecting the mass or concentration or the substance (such as the anemia state)—which parameters can be deteriorated by the volume of the distribution space or the actual hydration state—can be determined in an easy manner.

For example, in current practise it is unclear whether the unphysiologic concentration of a substance (e.g., very low hemoglobin levels of <8 g/dl) in a patient (e.g., with cardiac or renal impairment) should be corrected by modifying metabolism (e.g., by administering erythropoisesis stimulation agents) or by correcting its distribution volume or space (e.g., by ultrafiltration therapy or by administering diuretic drugs), or rather a combination of both. In other words, the measured Hb concentration may appear "artificially" altered or diluted, to different degrees, depending on the degree of overhydration (hyperhydration) or underhydration (hypohydration).

In case of severe overhydration, the blood volume may be expanded beyond normal levels, which leads to a decrease in Hb concentration even though the absolute red cell mass would be appropriate for a normal hydration status. As an example, an overhydration of 3 liter (L) may lead to an increase of 1 liter (L) in blood volume (BV) and, thus, 2 liter (L) in the interstitial space. Since the relative change in BV and OH is the same because of this typical 2:1 relationship it is possible to use values representing overhydration (which is more easily measurable than the blood volume) instead of blood volume for the criterion based evaluation. Assuming a typical blood volume (BV) of 5 L, this would represent an increase of 20%. A 20% decrease in Hb concentration would lead, e.g., from 11.5 to 9.2 g/dl. Such a low Hb level would lead to an increase in Erythropoietin (EPO) medication. Thus, the patient would possibly benefit more from a correction of his overhydration (OH) than from correction of Hb by means of pharmaceuticals.

All or some of the advantages mentioned above may also found when the present invention is applied to other substances than Hb which was only used here by way of example.

Other aspects, features, and advantages will be apparent from the description, figures, and claims. The following example relates to Hb as the substance in question and the distribution space is approximated by the measured relative overhydration of the patient, However, the present invention must not be understood to be limited to this example.

DETAILED DESCRIPTION OF THE DRAWINGS

Figure 1:
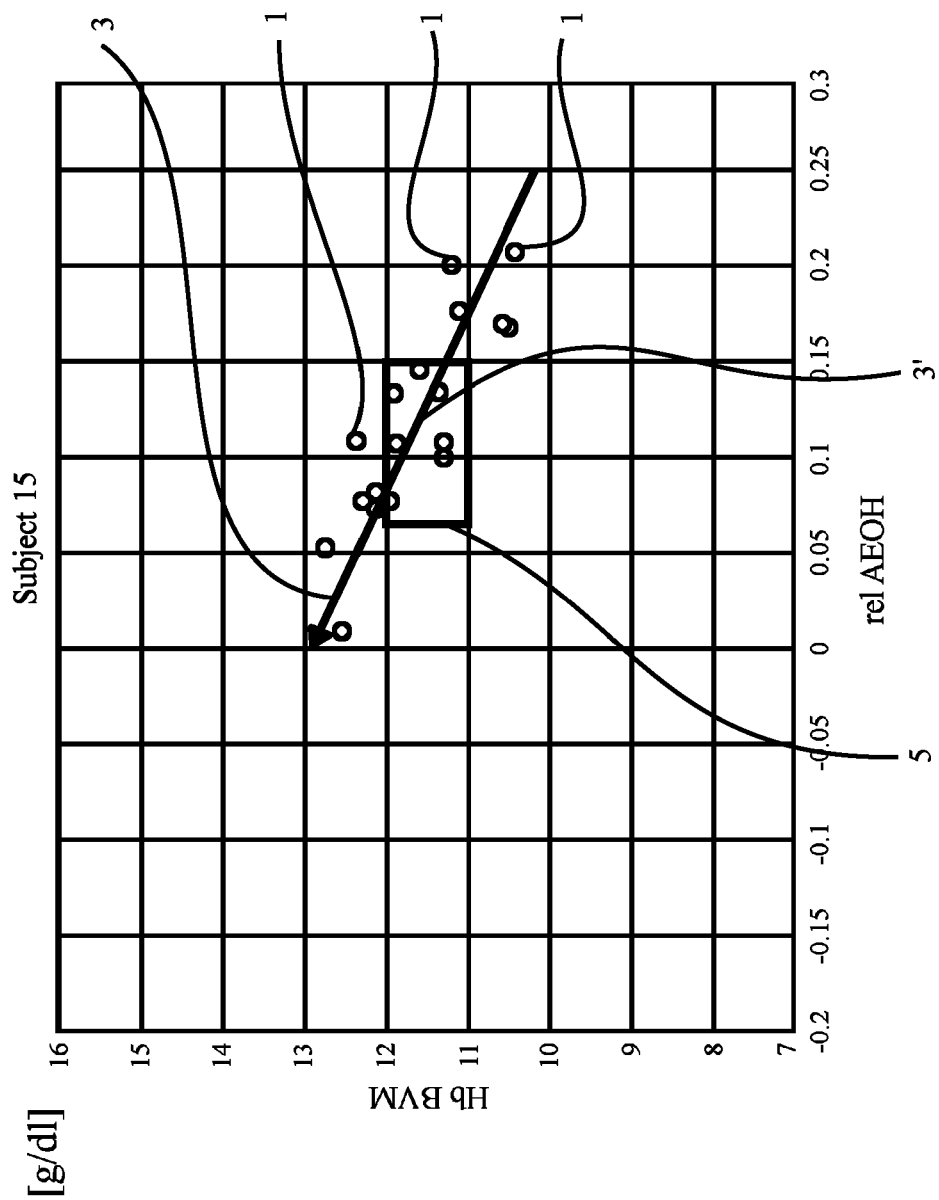
FIG. 1 shows a plot of states reflecting both an anemia state and a hydration state of the patient in a Hb-overhydration-diagram.

FIG. 1 shows the result of 19 measurements reflecting both the patient's anemia state and hydration state plotted in a diagram. The diagram is a Cartesian coordinate system showing Hb over relAEOH (relative overhydration, corrected for age). The results of the 19 measurements obtained from the patient in question (here anonymized as "Subject 15") are illustrated by means of small circles 1.

A regression analysis has been carried out based on the result of the 19 measurements. The obtained result has been added in FIG. 1 as regression line 3.

In FIG. 1, a target range 5 is further shown. The shape and position of target range 5 has been selected or determined based on experience and data of individuals by way of example. The invention must however not be understood to be limited to this. Both shape and position of the target range 5 can be determined differently if need should be. In particular, the target range can reflect findings from earlier measurement of the same patient. Further, the target range can reflect findings based on measurement of patients being a comparable situation as the patient at issue, e.g., suffer from the same disease.

The criterion to be fulfilled in the example of FIG. 1 is whether or not the regression line 3 crosses the target range 5 or not. As can be seen from FIG. 1, the criterion is clearly met in FIG. 1 as the regression line 3 obviously crosses the target range 5, see a portion 3' of regression line 3.

In the example of FIG. 1, the anemia state is reflected by Hb concentrations (in [g/dl]) obtained by means of any monitor as described in, e.g., "*Replacement of Renal Function by Dialysis*" by Drukker, Parson and Maher, Kluwer Academic Publisher, 5$^{th}$ edition, 2004, Dordrecht, The Netherlands, on pages 397 to 401 ("*Hemodialysis machines and monitors*") as is also noted above. Again, the respective disclosure of pages 397 to 401 is hereby incorporated by way of reference. The first value was obtained after a dialysis treatment has been started. It is noted that the monitor discussed here can be used for monitoring or detecting the blood volume (or changes thereof) with the blood volume being considered as another distribution space within the meaning of the present invention.

Also, in the example of FIG. 1, the hydration state is reflected by a relative overhydration (overhydration (OH) over extracellular water (ECW)), measured by means of a monitor as referred to above with reference to WO 2006/002685 A1. These values have been obtained before starting the dialysis treatment ("pre-Dx").

As regards any value referred to in here, time averaged values (as for Hb) can be used. Also, analysis revealed that the first value during treatment has the best correlation to weight changes and OH changes. The reason may be that towards the end of a treatment a lot of perturbation exists in the micro- and macrocirculation. It may be therefore that after 30 minutes without ultrafiltration (to make sure refilling has stopped) more reliable values can be measured.

Target range 5 may be understood as possible pre-Dx target range for both Hb and relOH.

As can be seen from FIG. 1, as the patient's hydration status was decreased, Hb concentration went up because of the (reversed) dilution effect; the red cell mass stayed constant, and so did the total Hb mass (not the concentration).

Since the regression line 3 which indicates a significant correlation between Hb and relOH moves trough the target range 5, a normalization of hydration by means of fluid management will automatically normalize Hb as well. Further interventions for managing the anemia state of the patient such as administration of EPO or an adoption thereof seem not to be necessary.

Figure 2:
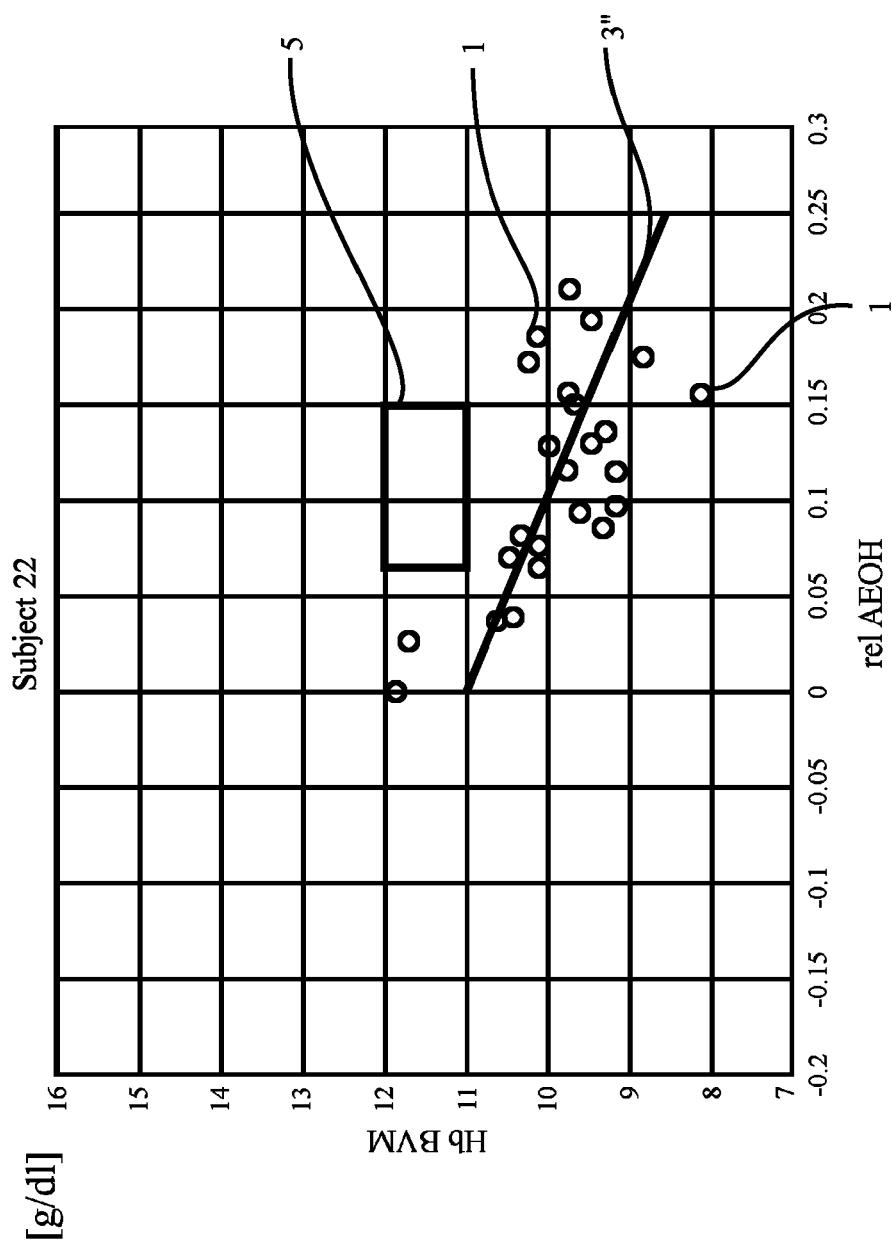
FIG. 2 shows a plot corresponding to the plot in FIG. 1, revealing data of another patient.

FIG. 2 shows a plot like that of FIG. 1, revealing data of another patient ("Subject 22"). In FIG. 2, the regression line 3" passes below the target range 5. The criterion applied here (i.e., the regression line 3 has to cross or intersect the target range 5) is not fulfilled. Hence, it appears that the values representing the anemia state of the patient will not return to normal once the hydration state has been brought back to normal. Hence, the patient will probably benefit from administration of substances increasing his Hb concentration back to normal, or from increasing the dosage of such substances if he already receives/takes medication.

Figure 3:
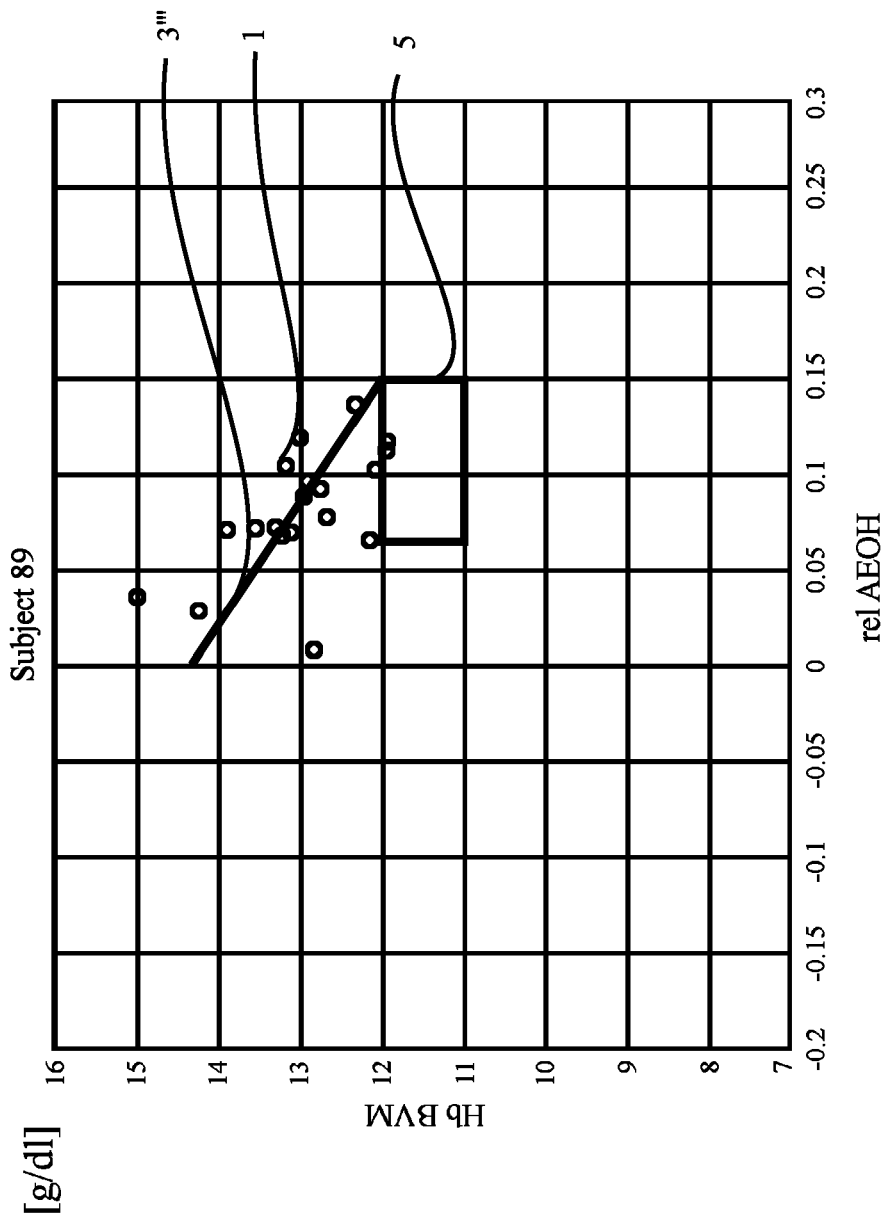
FIG. 3 shows a plot corresponding to the plot in FIG. 1, revealing data of another patient.

FIG. 3 shows a plot like those of FIG. 1 or FIG. 2, revealing data of yet another patient ("Subject 69"). In FIG. 3, the regression line 3'" passes above the target range 5. Again, the criterion applied here is not fulfilled. Again, it appears that the values representing the anemia state of the patient will not return to normal once the (over-)hydration state has been brought back to normal. Hence, in case the patient is being administered substances increasing his Hb concentration such as EPO, he most probably will benefit from reducing the dosage of those substances.

As can be seen from FIG. 3, the result of the evaluation of the anemia state of a patient according to the present invention depends very much on how the criterion is (pre-)determined. If, for instance, the criterion was defined to be fulfilled if only one, two or more results are found to be within a target range—instead of determining that a regression line has to intersect the target range as in the examples of the drawing—then the criterion had been fulfilled also in the example shown in FIG. 3.

Figure 4:
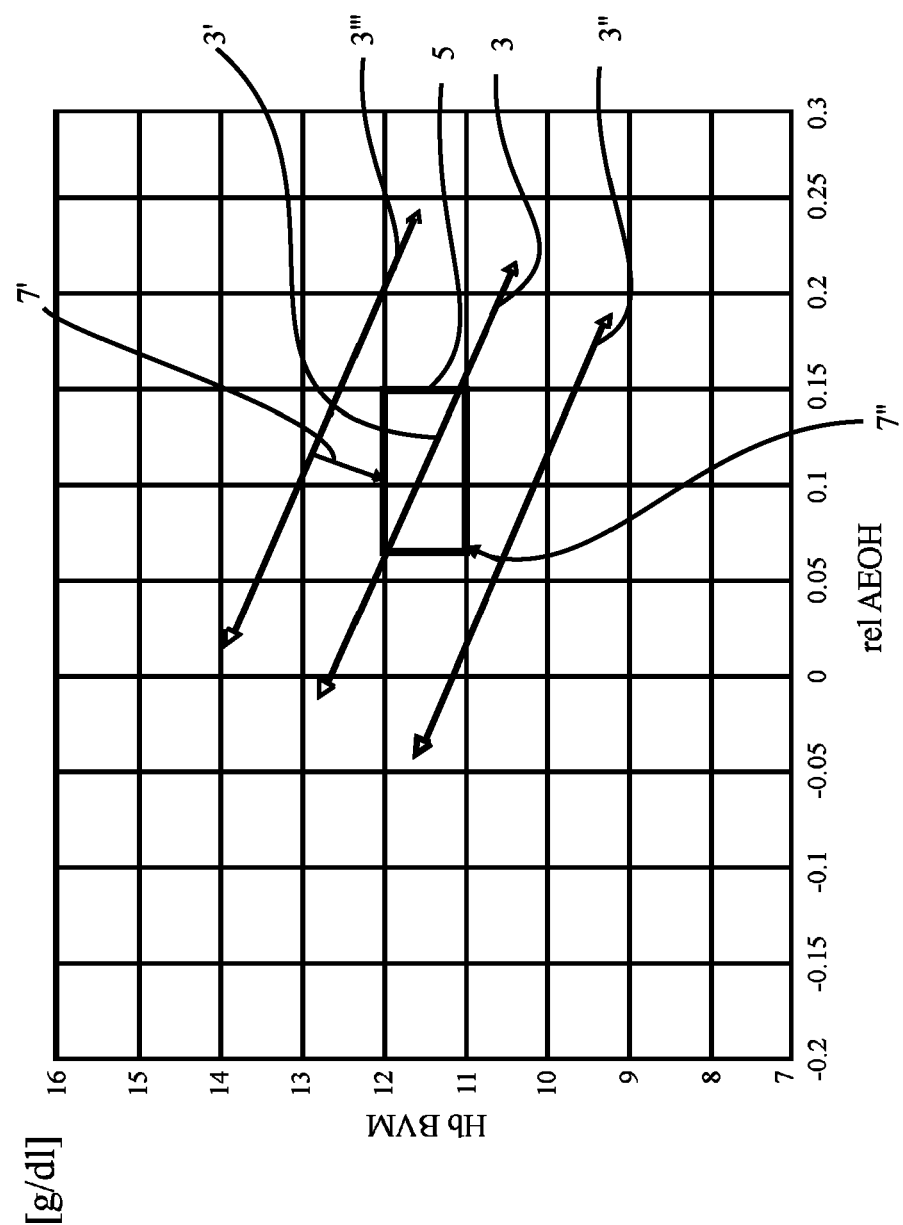
FIG. 4 shows a plot corresponding to the plot in FIG. 1 in a more general illustration.

What has been explained above with reference to FIG. 1 to FIG. 3 is schematically shown in FIG. 4 for any patient being administered EPO. FIG. 4 shows the general concept of how EPO dosage may be derived from the location (relative position) of the regression lines in the plot: If a regression line 3'" is found, it is advised to decrease the EPO dosage. A regression line calculated based on results of measurements done after adaption (decrease) of the EPO doses will be a lower one as indicated by arrow 7'. If a regression line 3" is found, the patient appears to benefit from high EPO doses. A regression line calculated based on results of measurements done after adaption (increase) of the EPO doses will be a higher one as indicated by arrow 7".

It is noted that for determining the regression line, only a few initial measurements are needed—already one result or point may be enough. Results obtained from measurements done over a period of time of, e.g., 2-4 weeks will be sufficient.

Figure 5:
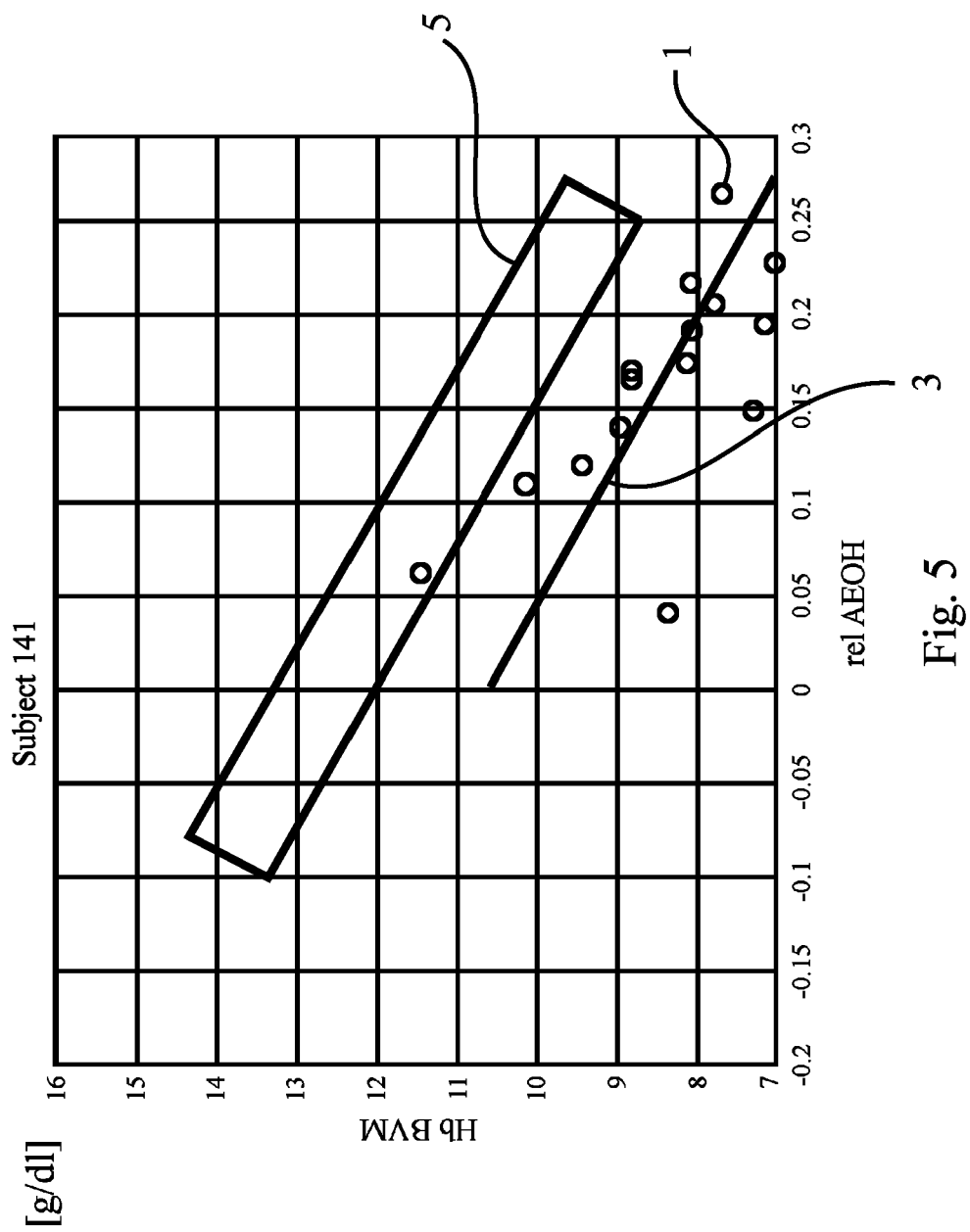
FIG. 5 shows a plot corresponding to the plot in FIG. 1, revealing data of yet another patient.
Figure 6:
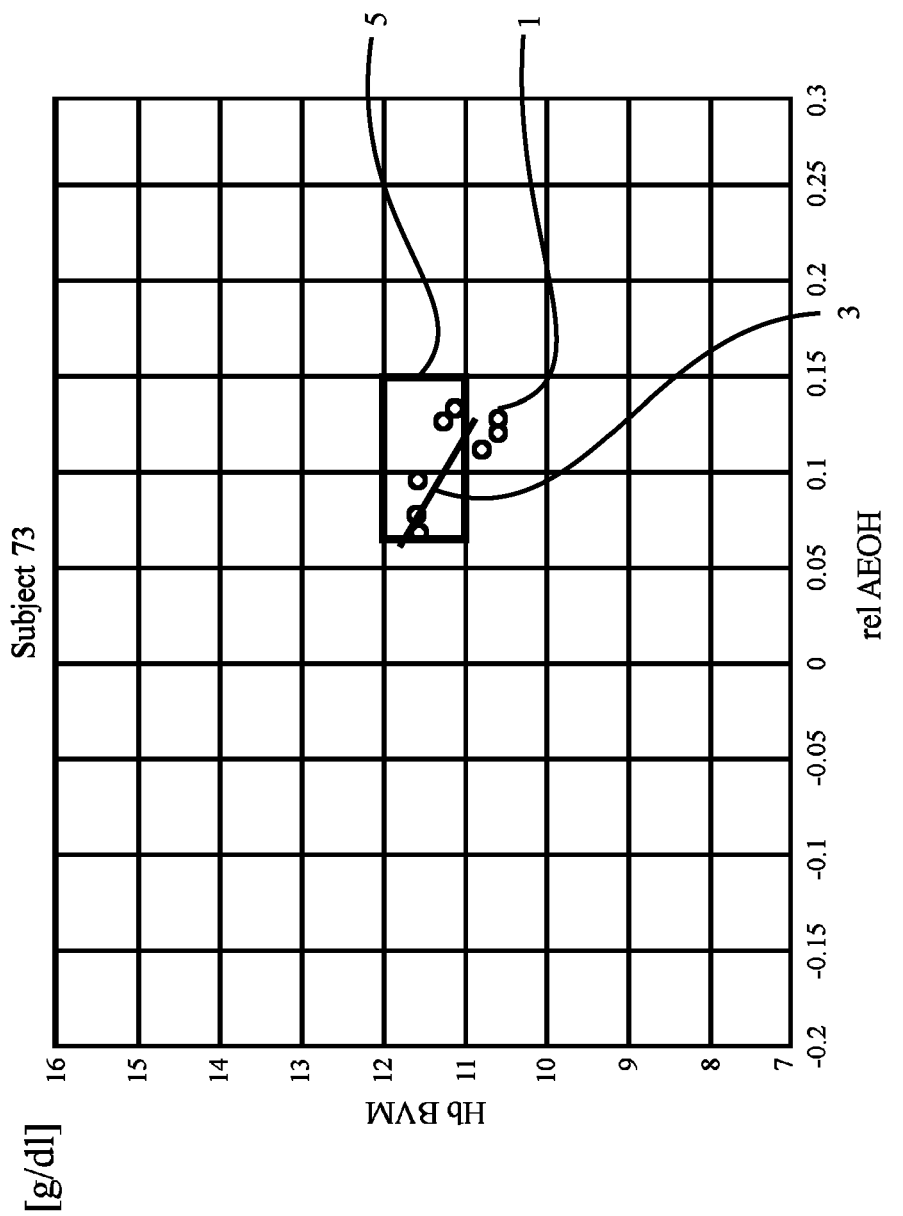
FIG. 6 shows a plot corresponding to the plot in FIG. 1, revealing data of yet another patient.
Figure 7:
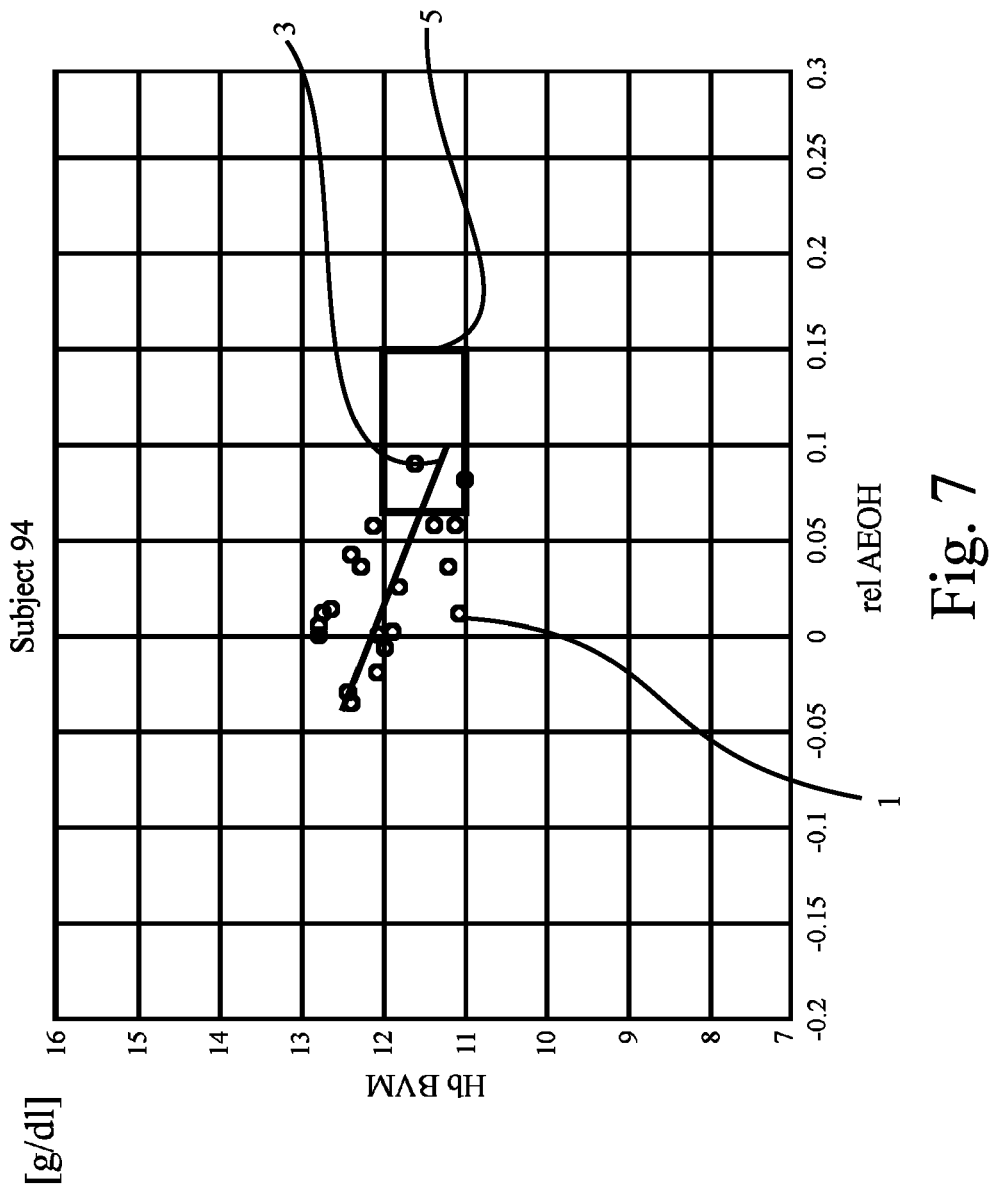
FIG. 7 shows a plot corresponding to the plot in FIG. 1, revealing data of yet another patient.
Figure 8:
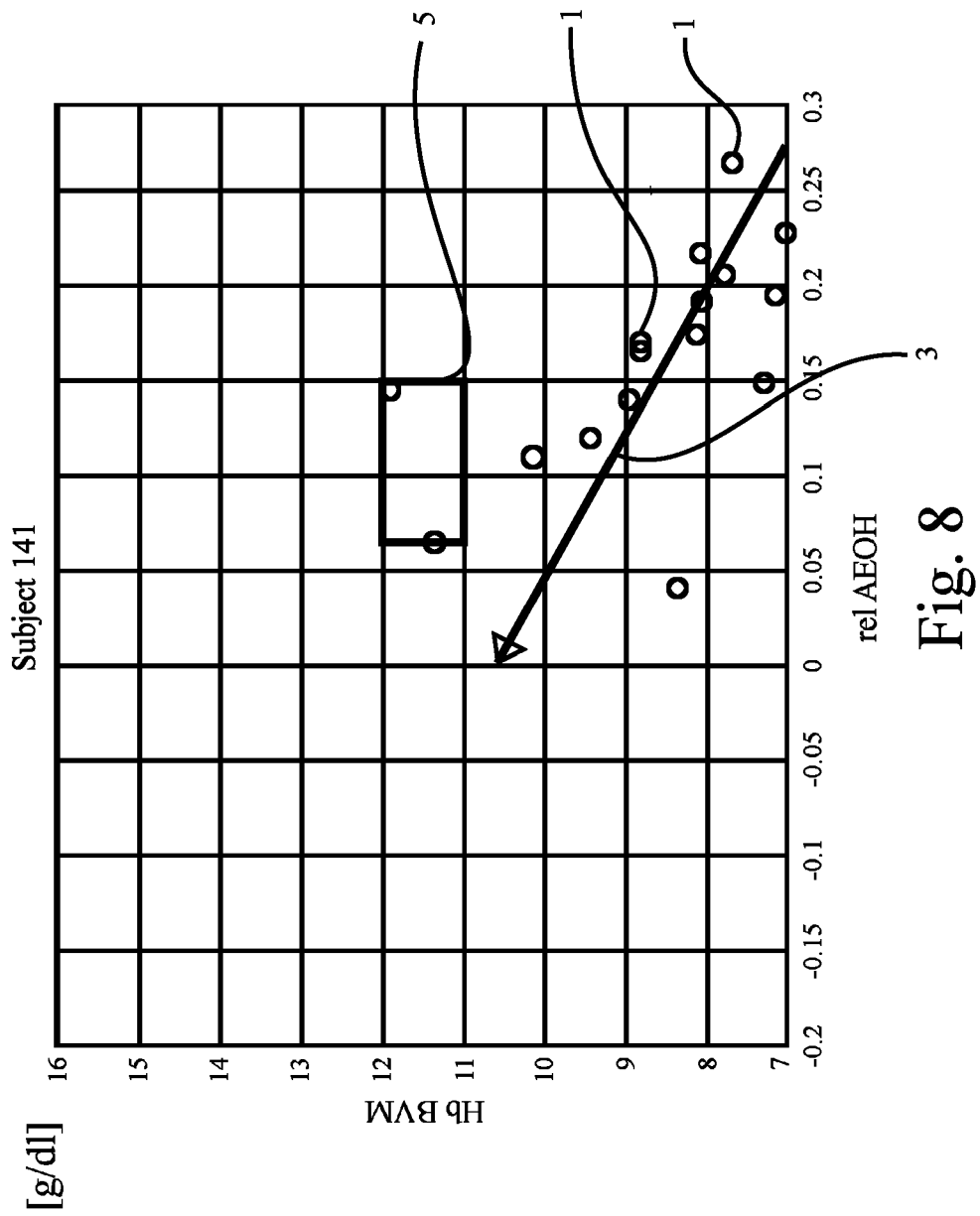
FIG. 8 shows a plot corresponding to the plot in FIG. 1, revealing data of the patient of FIG. 5.
Figure 9:
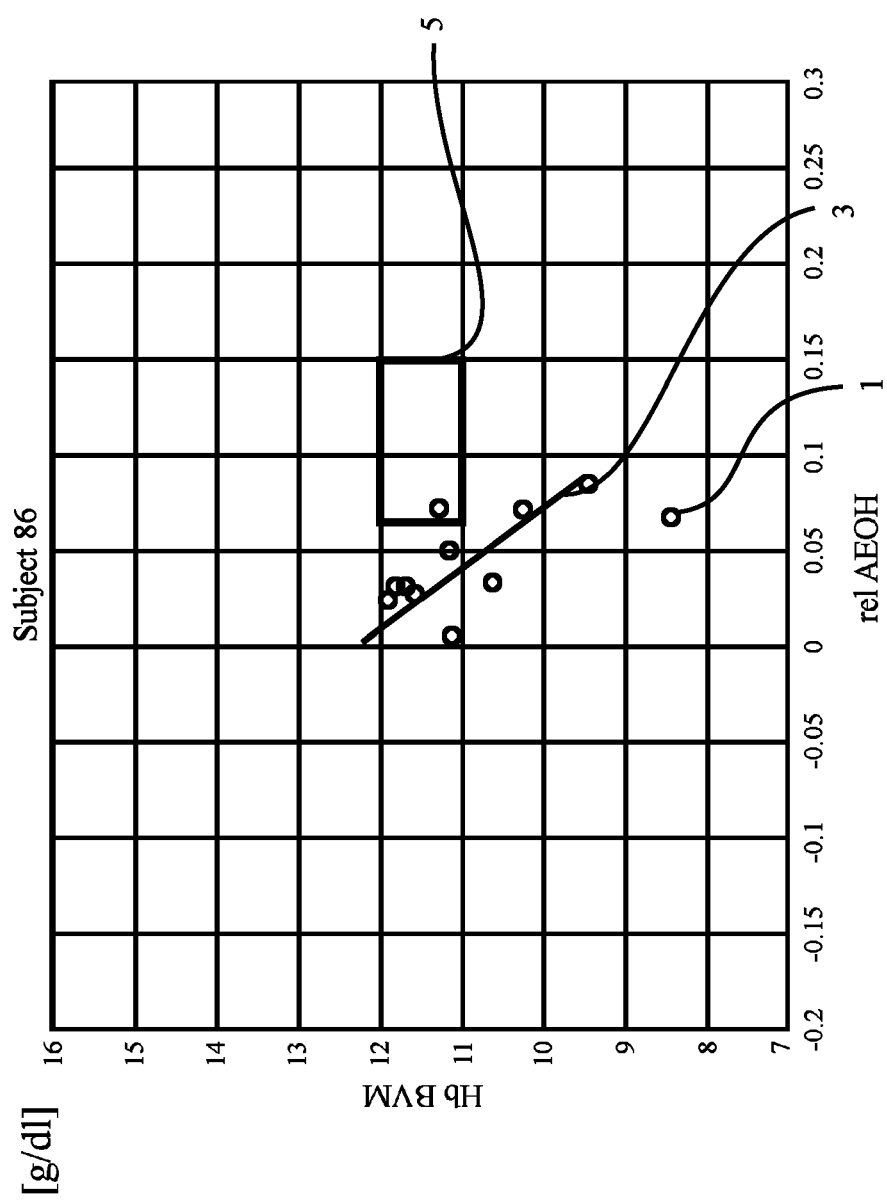
FIG. 9 shows a plot corresponding to the plot in FIG. 1, revealing data of yet another patient.

As has been indicated in FIG. 5 by the shape of the target range 5, with the shape of FIG. 5 being different to those of FIG. 1 to FIG. 4, it is even possible to define a "target corridor 5'" for the dosage of a pharmaceutical such as EPO. The target corridor 5' is a more specific example of the target range 5 known from FIG. 1 to FIG. 4. It differs in that it has been adapted to the individual regression line slope of the patient in question (here: of "Subject 141"). Shaped as shown in FIG. 5, the target corridor 5' may contribute to allow early adjustment of EPO even when normal hydration status has not yet been reached. This may be particularly beneficial in respect of long time constants between EPO administration and production of red blood cells (hematopoiesis). As can be seen from FIG. 5, EPO dosage may be increased already at the beginning of the dry-out-phase.

As can be seen from FIG. 5, the criterion for evaluating the anemia state of a patient to be fulfilled according to the present invention can also be whether or not the slope or inclination of the regression line is parallel to the extension or the main extension of a target range, in particular of a rectangular one. Also, the criterion can be whether the regression line falls completely within the target range, or whether the regression line does not cross certain, predetermined portions or sides of the target range and so forth.

FIG. 6 to FIG. 9 show further examples of plots drawn from the results of Hb and hydration measurements obtained from yet other patients ("Subjects 73, 86, and 94") and the patient of FIG. 5. The preset criterion (i.e., the regression line 3 has to cross or intersect the target range 5) is not fulfilled for the patients of FIG. 8 and FIG. 9, whereas it is fulfilled for the patients of FIGS. 6 and 7.

From the figures it can be seen that if the patient's reference line or regression line crosses the reference range only the hydration state should be adjusted—if the reference or regression line passes above or below, metabolic processes should be addressed (e.g., with EPO).

Figure 10:
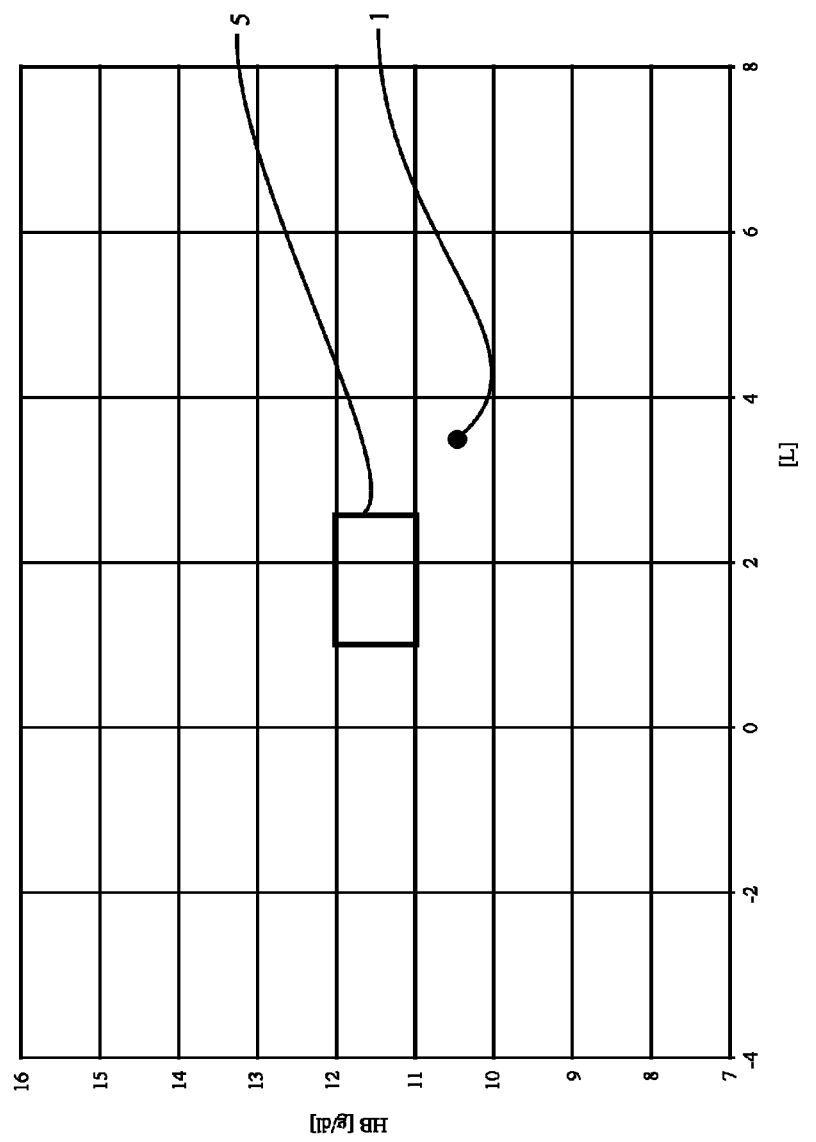
FIG. 10 shows a plot corresponding to that of FIG. 1, revealing data of only one measurement.

FIG. 10 shows a plot like those of FIG. 1 or FIG. 2 displaying the concentration of Hb [g/dl] over overhydration [L, or l], revealing data of only one measurement being depicted by circle 1. As can be seen from FIG. 10, no regression line 3 can be determined based on only one measurement. From FIG. 10 it is further understood that in certain circumstances no regression line is required for assessing whether or not the criterion (here: the measurement represented by circle 1 falls into the range 5 or not) is fulfilled. In any case, in the example of FIG. 10 the preset criterion is not fulfilled.

As can be seen from any of the figures discussed above, whether the criterion is met by certain anemia states and hydration states of the respective patient depends on how the criterion is set or determined beforehand.

Figure 11:
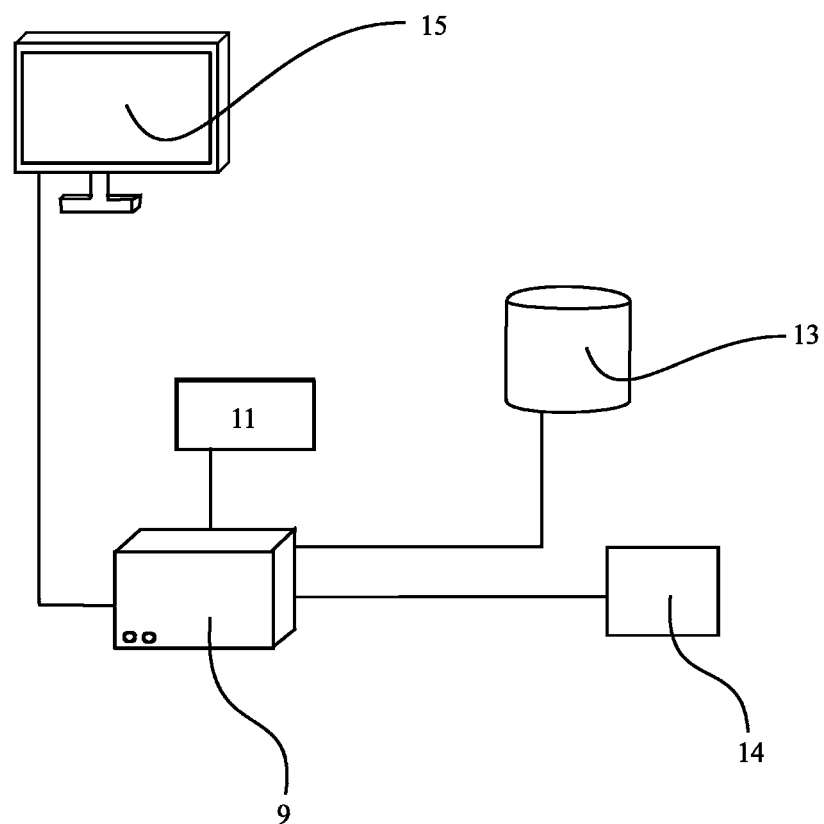
FIG. 11 shows a first apparatus comprising a controller for carrying out the method according to the present invention.

FIG. 11 shows an apparatus 9 comprising a controller 11 for carrying out the method according to the present invention. The apparatus 9 is connected to an external database 13 comprising the results of measurements and the data needed for the method according to the present invention. The database 13 can also be an internal means. The apparatus 9 may optionally have means 14 for inputting data into the controller 11 or into the apparatus 9. Such data may be information about the mass, the volume, the concentration of the substance as is set forth above. Such data input into the apparatus 9 may—additionally or instead—also be information about the distribution space of the patient or an approximation thereof. Also, the criterion may be inputted by means of the input means 14. The criterion may, however, alternatively be stored in database 13 or any other storage. The criterion may be calculated or determined by the controller 11 or any other item comprised by the apparatus 9 or interconnected to it. The results of the evaluation, calculation, comparison, assessment etc. performed by the controller 11 and/or the apparatus 9 can be displayed on the monitor 15 or plotted by means of a—not displayed but optionally also encompassed—plotter or stored by means of the database 13 or any other storage means. The database 13 can also comprise a computer program initiating the method according to the present invention when executed.

In particular, the controller 11 can be configured for determining a relation between one or more calculated or measured value(s) reflecting the mass or the concentration or the volume of the substance comprised by a tissue or a bodily fluid and a distribution space of the patient or an approximation thereof, and for assessing whether the relation fulfils at least one predetermined criterion.

Figure 12:
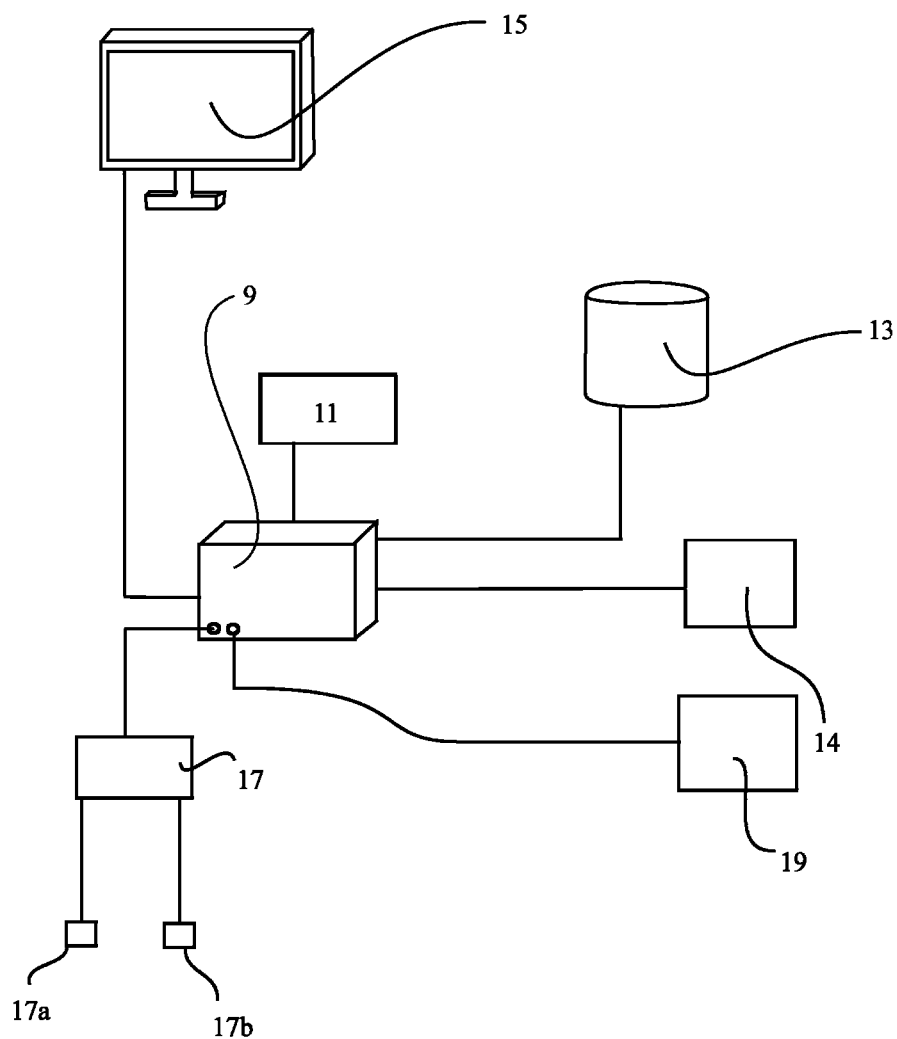
FIG. 12 shows a second apparatus comprising a controller for carrying out the method according to the present invention.

As can be seen from FIG. 12, for corresponding measurements, the apparatus 9 can be connected (by means of wires or wireless) with a bioimpedance measurement means 17 as one example of a means for measuring or calculating the hydration state or an overhydration state. Generally, the means for measuring or calculating the hydration state or an overhydration state can be provided in addition to the external database 13 comprising the results of measurements and the data needed for the method according to the present invention, or in place of the external database 13 (that is, as an substitute).

The bioimpedance measurement means 17 can be capable of automatically compensating for influences on the impedance data like contact resistances.

An example for such a bioimpedance measurement means 17 is a device from Xitron Technologies, distributed under the trademark Hydra™ that is further described in WO 92/19153, the disclosure of which is hereby explicitly incorporated in the present application by reference.

The bioimpedance measurement means 17 may comprise various electrodes. In FIG. 12, only two electrodes 17a and 17b shown which are attached to the bioimpedance measurement means 17. Additional electrodes are, of course, also contemplated.

Each electrode implied can comprise two or more ("sub"-)electrodes in turn. Electrodes can comprise a current injection ("sub"-)electrode and a voltage measurement ("sub"-)electrode. That is, the electrodes 17a and 17b shown in FIG. 12 can comprise two injection electrodes and two voltage measurement electrodes (i.e., four electrodes in total).

Generally spoken, the means for measuring or calculating the hydration state or an overhydration state can be provided by means of weighing means, a keyboard, a touch screen etc. for inputting the required data, sensors, interconnections or communication links with a lab, any other input means, etc.

Similarly, the apparatus 9 may have means 19 for measuring or calculating means for obtaining a value reflecting the mass, the volume or the concentration of the substance that can again be provided in addition to the external database 13 already comprising the results of measurements and the data needed for the method according to the present invention, or in place of the external database 13 (that is, as an substitute).

The means 19 can be provided as a weighing means, a keyboard, touch screen etc. for inputting the required data, sensors, interconnections or communication links with a lab, a Hb concentration probe, any other input means, etc.

Again, it is noted that the figures relate to Hb/anemia state and relOH/hydration state by means of examples showing how one embodiment according to the present invention may be carried out. They are not to be understood as limiting.

What is claimed is:
1. A method for evaluating a value representing a mass or a concentration or a volume of a substance contained in a tissue or a bodily fluid of a patient, comprising the steps of:
measuring the value representing the mass or the concentration or the volume of the substance contained in the tissue or the bodily fluid of the patient;

determining, by a processor, a relation between:
(a) the measured value representing the mass or the concentration or the volume of the substance contained in the tissue or the bodily fluid of the patient, and
(b) a distribution space of the patient, the distribution space being a body fluid, a body tissue, a body weight, a total body mass, a combination of the body fluid and the body tissue, or a space of the patient, wherein the distribution space is based on calculated or measured values reflecting a relative overhydration (relOH) of the patient or an absolute overhydration (OH) of the patient;

assessing, by the processor, whether the relation fulfils at least one criterion; and based on the assessing whether the relation fulfills the at least one criterion, adjusting the distribution space of the patient using dialysis.

2. The method according to claim 1, wherein the one or more calculated or measured value(s) reflecting the mass, the volume or the concentration of the substance was obtained from a sample selected from the group consisting of blood samples, urine samples, and tissue samples.

3. The method according to claim 1, wherein the substance is selected from the group consisting of proteins produced naturally in the body of the patient, hemoglobin, albumin, insulin, glucose, C-reactive protein (CRP), and pharmaceutically-effective non-endogeneous substances.

4. The method according to claim 1, wherein the mass or the concentration of the substance or changes thereof is an indicator of an anemia state of the patient.

5. The method according to claim 4, wherein the indicator of the anemia state of the patient is selected from the group consisting of a concentration of hemoglobin, a total mass of hemoglobin, a change in the concentration or in the total mass of hemoglobin over time, a hematocrit, and a change in the hematocrit over time.

6. The method according to claim 1, wherein the distribution space of the patient is selected from a measured value of a blood volume or a calculated value of the blood volume.

7. The method according to claim 1, wherein the distribution space is measured or approximated before a dialysis treatment or based on pre-dialysis values of the patient.

8. The method according to claim 1, further comprising the step of:
defining a target range in a diagram reflecting (a) the mass or the concentration of the substance or the approximation thereof and (b) the distribution space or the approximation thereof.

9. The method according to claim 8, further comprising the step of:
calculating a regression line based on either the measured or the calculated values reflecting both (a) the mass or the concentration of the or an approximation thereof, and (b) the distribution space of the patient or an approximation thereof; and
determining any overlap between the regression line and the target range.

10. The method according to claim 1, further comprising the step of:
at least one of calculating or measuring the values reflecting at least one of (a) the mass or the concentration of the substance or an approximation thereof or (b) the distribution space of the patient or an approximation thereof.

11. The method according to claim 1, further comprising the step of:
determining the at least one criterion.

12. The method according to claim 1, wherein the distribution space is measured or approximated during or after a dialysis treatment.

13. A system for evaluating a value representing a mass or a concentration or a volume of a substance contained in a tissue or a bodily fluid of a patient, comprising a controller configured to:
measure the value representing the mass or the concentration or the volume of the substance contained in the tissue or the bodily fluid of the patient;
determine a relation between:
(a) the measured value representing the mass or the concentration or the volume of the substance contained in the tissue or the bodily fluid of the patient, and
(b) a distribution space of the patient, the distribution space being a body fluid, a body tissue, a body weight, a total body mass, a combination of the body fluid and the body tissue, or a space of the patient, wherein the distribution space is based on calculated or measured values reflecting a relative overhydration (relOH) of the patient or an absolute overhydration (OH) of the patient;
assess whether the relation fulfils at least one criterion; and
based on the assessing whether the relation fulfills the at least one criterion, adjust the distribution space of the patient using dialysis.

14. The system according to claim 13, further comprising a system configured to obtain a value reflecting a characteristic selected from the group consisting of the distribution space of the patient's body, the approximation of the distribution space of the patient's body, changes in the distribution space of the patient's body, the mass of the substance, changes in the mass of the substance, the volume of the substance, changes in the volume of the substance, the concentration of the substance, and changes in the concentration of the substance.

15. The system according to claim 14, wherein the system configured to obtain the value comprises a device configured to measure or calculate a hydration state or a degree of overhydration of the patient.

16. The system according to claim 14, wherein the system configured to obtain the value comprises a device selected from the group consisting of a device configured to measure weight, a device for configured to determine a blood volume of the patient, a keyboard, a touch screen, and a device configured to measure or calculate at least one of the concentration, the volume or the mass of the substance.

17. The system according to claim 13, further comprising an output device configured to output results provided by the controller.

18. The system according to claim 13, wherein the system is configured to treat a patient's blood.

19. The system according to claim 18, wherein the system is configured to treat the patient's blood by dialysis.

20. The system according to claim 19, wherein the system is configured to treat the patient's blood by at least one of hemofiltration, ultrafiltration, or hemodialysis.

21. A non-transitory computer-readable medium with an executable program stored thereon, wherein the program instructs a programmable computer system to perform the following steps for evaluating a value representing a mass or a concentration or a volume of a substance contained in a tissue or a bodily fluid of a patient:

measuring the value representing the mass or the concentration or the volume of the substance contained in the tissue or the bodily fluid of the patient;

determining a relation between:

(a) the measured value representing the mass or the concentration or the volume of the substance contained in the tissue or the bodily fluid of the patient, and (b) a distribution space of the patient, the distribution space being a body fluid, a body tissue, a body weight, a total body mass, a combination of the body fluid and the body tissue, or a space of the patient, wherein the distribution space is based on calculated or measured values reflecting a relative overhydration (relOH) of the patient or an absolute overhydration (OH) of the patient;

assessing whether the relation fulfils at least one criterion; and based on the assessing whether the relation fulfills the at least one criterion, adjusting the distribution space of the patient using dialysis.

22. The method according to claim 1, further comprising:
based on the assessing whether the relation fulfills the at least one criterion, adjusting a dosage of a medicament that is to be administered to the patient for improving an anemia state of the patient.

23. The method according to claim 1, wherein the distribution space is adjusted by: (i) ultrafiltration, (ii) administration of pharmaceutically effective substances, or (iii) both ultrafiltration and administration of pharmaceutically effective substances.

24. The method according to claim 1, wherein the distribution space is adjusted by administering pharmaceutically effective substances comprising diuretics to the patient.

* * * * *